(12) United States Patent
Damodaran et al.

(10) Patent No.: US 10,952,952 B2
(45) Date of Patent: *Mar. 23, 2021

(54) SKIN LIGHTENING COMPOSITION

(71) Applicant: Conopco, Inc., Englewood Cliffs, NJ (US)

(72) Inventors: Anita Damodaran, Bangalore (IN); Manoj Kumar Joshi, Bangalore (IN); Balu Kunjupillai, Nagapattinam (IN); Rezwan Shariff, Andhra Pradesh (IN)

(73) Assignee: Conopco, Inc., Englewood Cliffs, NJ (US)

( * ) Notice: Subject to any disclaimer, the term of this patent is extended or adjusted under 35 U.S.C. 154(b) by 29 days.

This patent is subject to a terminal disclaimer.

(21) Appl. No.: 15/764,968

(22) PCT Filed: Oct. 4, 2016

(86) PCT No.: PCT/EP2016/073617
§ 371 (c)(1),
(2) Date: Mar. 30, 2018

(87) PCT Pub. No.: WO2017/060211
PCT Pub. Date: Apr. 13, 2017

(65) Prior Publication Data
US 2018/0280278 A1  Oct. 4, 2018

(30) Foreign Application Priority Data
Oct. 5, 2015  (EP) .................................... 15188360

(51) Int. Cl.
*A61K 8/67* (2006.01)
*A61K 8/49* (2006.01)
*A61Q 15/00* (2006.01)
*A61Q 17/00* (2006.01)
*A61Q 19/02* (2006.01)
*A61Q 19/10* (2006.01)

(52) U.S. Cl.
CPC ............ *A61K 8/675* (2013.01); *A61K 8/4926* (2013.01); *A61Q 15/00* (2013.01); *A61Q 17/005* (2013.01); *A61Q 19/02* (2013.01); *A61Q 19/10* (2013.01); *A61K 2800/70* (2013.01)

(58) Field of Classification Search
None
See application file for complete search history.

(56) References Cited

U.S. PATENT DOCUMENTS

| 5,411,741 | A | 5/1995 | Zaias |
| 5,582,817 | A | 12/1996 | Otsu |
| 8,084,049 | B2 | 12/2011 | Weidner |
| 9,227,090 | B2 | 1/2016 | Madison |
| 2003/0203943 | A1 | 10/2003 | Weidner |
| 2009/0105188 | A1 | 4/2009 | Giannone et al. |
| 2018/0280278 | A1 | 10/2018 | Damodaran |

FOREIGN PATENT DOCUMENTS

| CN | 103976889 | 8/2014 |
| CN | 105682748 | 6/2016 |
| EP | 1283033 | 2/2003 |
| EP | 2522331 | 11/2012 |
| EP | 2742942 | 6/2014 |
| JP | 2003267817 | 9/2003 |
| JP | 2004123554 | 4/2004 |
| JP | 2005537238 | 12/2005 |
| WO | WO947141 | 9/1999 |
| WO | WO2004000333 | 12/2003 |
| WO | WO2010002586 | 1/2010 |
| WO | WO2011133692 | 10/2011 |
| WO | WO2013030794 | 3/2013 |
| WO | WO2015061512 | 4/2015 |
| WO | WO2015172801 | 11/2015 |

OTHER PUBLICATIONS

JP 2003-267817_machine translation (Year: 2003).*
Written Opinion2 in PCTEP2016073626; dated Sep. 19, 2017.
Search Report and Written Opinion in PCTEP2016073626; dated Feb. 28, 2017.
Co-Pending Application, U.S. Appl. No. 15/765,015.
Hakozaki et al., The effect of niacinamide on reducing cutaneous pigmentation and suprression of melanosome transfer, British Journal of Dermatology, 2002, pp. 20-31; XP002333293, vol. 147, No. 1.
IPRP2 in PCTEP2016073617, Oct. 5, 2017.
Nikitakis et al., Picolinamide, International Cosmetic Ingredient Dictionary and Handbook, 2014, p. 2623; XP002767164, 15th Edition, vol. 2.
Pourahmadi Mohammad et al., Evaluation of the Effect of Topical Picolinamide on Epidermal Melasma, Biosciences Biotechnology Research Asia, 2014, pp. 1047-1050, vol. 11 No. 2.
Search Report & Written Opinion in EP15188360, dated May 17, 2016.
Search Report & Written Opinion in PCTEP2016073617, dated Feb. 13, 2017.
Hongli Sun et al.; Field-amplified sample injection for the determination; Analytical Methods; 2013; pp. 5615-5621; 5.
IPRP2 in PCTEP2016073626; Jan. 2, 2018.

(Continued)

*Primary Examiner* — Jake M Vu
(74) *Attorney, Agent, or Firm* — Ellen Plotkin

(57) ABSTRACT

The present invention is in the field of personal care compositions; in particular skin lightening compositions. It is believed that niacinamide reduces the melanosome transfer from melanocytes to keratinocytes thereby bringing about skin lightening. However, niacinamide is known to have little or no effect directly on the melanin content in the melanocytes. Thus a composition with multiple modes of action, that combines the reduction of melanosome transfer and the reduction of melanin content in the melanocytes remains to be desired. It is therefore an object of the present invention to provide a composition with synergistic amounts of picolinamide and niacinamide, providing improved melanosome transfer inhibition. It has been found that a synergistic skin lightening effect is obtained when niacinamide is combined with its isomer, picolinamide.

8 Claims, No Drawings

(56) References Cited

OTHER PUBLICATIONS

M.H. Braff and R.L. Gallo; Antimicrobial Peptides; An Essential Component of the Skin Defensive Barrier; 2006; pp. 1-20; vol. 306:91-100; Springer-Verlag Berlin Heidelberg.
Pierre Kyme et al.; C/EBP epsilon mediates nicotinamide-enchanced clearance of *Staphylococcus aureus* in mice; Journal of Clinical Investigation; Sep. 4, 2012; pp. 3316-3329; ; vol. 122, No. 9; United States of America.

\* cited by examiner

SKIN LIGHTENING COMPOSITION

Under Request for Continued Application procedure (RCE), this is a continuing application of Ser. No. 15/164,968 filed Mar. 30, 2018.

FIELD OF THE INVENTION

The present invention is in the field of personal care compositions; in particular skin lightening compositions.

BACKGROUND OF THE INVENTION

Most people are concerned with the degree of pigmentation of their skin. For example, people with age spots or freckles may wish such pigmented spots to be less pronounced, while others may wish to reduce the skin darkening caused by exposure to sunlight or to lighten their natural skin colour. To meet this need, many attempts have been made to develop products that reduce the pigment production in the melanocytes. However, the substances identified thus far tend to have either low efficacy or undesirable side effects, such as, for example, toxicity or skin irritation. Therefore, there is a continuing need for new cosmetic skin lightening agents, with improved overall effectiveness.

Conventional skin lightening compositions are based on the use of skin lightening agents that are believed to control dispersion of melanin or inhibit tyrosinase. These skin-lightening agents include niacinamide, carboxylic acids like azelaic acid and kojic acid, plant extracts, hydroquinone etc. Niacinamide is one of the widely used skin lightening agents in compositions for topical application.

Niacinamide is the amide form of vitamin B3 (Niacin). Vitamin B3 is an essential water-soluble vitamin and is found in the form of niacin or niacinamide in a wide variety of food including meat, fish, legumes, nuts, grains, mushrooms, yeast & coffee. It is implicated in various cellular functions like DNA repair, keratinocyte differentiation, lipid synthesis, pigmentation and inflammation, most important of them being in cellular bioenergetics. Niacinamide in the form of pyridine nucleotide, nicotinamide adenine dinucleotide (NAD) is important for energy metabolism. A diet deficient in B3 leads to disease called Pellagra characterized by skin conditions with dermatitis and pigmentation. This was the observation that led to the discovery of niacinamide as a skin lightening agent four decades ago.

It is believed that niacinamide reduces the melanosome transfer from melanocytes to keratinocytes thereby bringing about skin lightening. However, niacinamide is known to have little or no effect directly on the melanin content in the melanocytes.

A composition with multiple modes of action, that combines the reduction of melanosome transfer and the reduction of melanin content in the melanocytes remains to be desired.

WO 2013/030794 relates to skin and/or hair depigmentation compositions comprising a pyridine derivative and dermatologically acceptable carriers. This document discloses picolinamide, preferably in a concentration of 0.001 to 30% by weight. WO 2013/030794 further discloses that the composition may include a skin and/or hair benefit agent from a list of agents including nicotinamide.

It is therefore an object of the present invention to provide a composition with synergistic amounts of picolinamide and niacinamide, providing improved melanosome transfer inhibition.

It is a further object of the invention to achieve a high melanosome transfer inhibition at low concentration of actives.

It is a further object of the invention to achieve a reduction of melanin content in the melanocytes at lower concentration of actives.

Without wishing to be bound by a theory, it is thought that although picolinamide, is not a precursor for NAD+, it may have an effect on the various processes involved in pigmentation.

Without wishing to be bound by theory, it is thought that unlike niacinamide which has shown to affect the melanosome transfer, picolinamide has an effect on the melanin production with little or no effect of melanosome transfer. The invention thus relates to a composition comprising a synergistic combination of niacinamide and picolinamide for use in skin lightening.

It has been found that a synergistic skin lightening effect is obtained when niacinamide is combined with its isomer, picolinamide.

SUMMARY OF THE INVENTION

Accordingly, in a first aspect, the invention provides a skin lightening composition comprising 0.1 to 10% by weight of picolinamide; and 0.1 to 10% by weight of niacinamide.

In a second aspect, the invention provides use of the composition according to the invention for skin lightening.

In a third aspect, the invention provides a method of lightening the skin of a human, the method comprising the step of applying the composition according to the invention onto the skin.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

In a first aspect of the invention, a skin lightening composition is provided, the composition comprising niacinamide and picolinamide.

Niacinamide

Niacinamide, also known as nicotinamide and as pyridine-3-carboxamide is the active, water soluble form of vitamin B3. It is essential to the coenzymes NADH and NADPH and therefore for over 200 enzymatic reactions in the body including ATP formation.

Niacinamide is present in the composition of the present invention in a concentration of 0.1 to 10%, preferably 0.5 to 9%, more preferably 1 to 8%, still more preferably 2 to 7%, even more preferably 3 to 8%, yet more preferably 4 to 7%, or even 5 to 6% by weight of the composition.

Picolinamide

Nicotinamide, a pyridine 3-carboxamide has 2 other positional isomers by substitution at 2, and 4 position of the pyridine ring, picolinamide (pyridine 2-carboxamide) and isonicotinamide (pyridine 4-carboxamide) respectively.

The synergistic skin lightening effect of the present invention is obtained by niacinamide in combination with picolinamide (pyridine 2-carboxamide), the positional isomer by substitution at 2 position of the pyridine ring.

Picolinamide is present in the composition of the present invention in a concentration of 0.1 to 10%, preferably 0.5 to 9%, more preferably 1 to 8%, still more preferably 2 to 7%, even more preferably 3 to 8%, yet more preferably 4 to 7%, or even 5 to 6% by weight of the composition.

Molar Ratio of Picolinamide to Niacinamide

The synergistic skin lightening effect is obtained at a picolinamide to niacinamide molar ratio of not more than 20:1, preferably not more than 16:1, more preferably not more than 10:1, still more preferably not more than 8:1, even more preferably not more than 4:1.

Preferably, molar ratio of picolinamide to niacinamide is at least 10:1, more preferably at least 8:1, still more preferably at least 4:1, even more preferably at least 2:1, further more preferably at least 1:1 and most preferably at least 1.25:1.

Preferably, molar ratio of picolinamide to niacinamide is from 20:1 to 1:20, preferably from 16:1 to 1:16, more preferably from 10:1 to 1:10, still more preferably from 8:1 to 1:8, even more preferably from 4:1 to 1:4, further more preferably from 2:1 to 1:2 and most preferably from 1.25:1 to 1:1.25.

For best results on melanosome transfer inhibition, the molar ratio of picolinamide to niacinamide is not more than 2:1, preferably not more than 1.25:1.

Other Actives

The skin lightening compositions of the present invention may further include another skin benefit agent preferably selected from the group comprising hydroxy acids, polyhydroxy acids, hydroxy fatty acids in particular 12-hydroxy stearic acid, kojic acid, depigmenting oligopeptides, galardin, polyphenol antioxidants, thiolic antioxidants, cysteamine hydrochloride, hydroquinone, t-butyl hydroquinone, vitamin C derivatives, vitamin E derivatives, vitamin B derivatives, retinoids, 4-substituted resorcinol derivatives, and mixtures thereof.

Optional Ingredients

The composition of the present invention may further comprise a cosmetically acceptable vehicle which may act as diluents, dispersants and/or carriers for the skin lightening agents used in the composition, so as to facilitate their distribution when the composition is applied to the skin. The cosmetically acceptable vehicle suitable for use in the present invention may be aqueous, anhydrous or an emulsion; aqueous or an emulsion, especially water-in-oil or oil-in-water emulsion being most preferred. Water when present typically makes up the balance of the composition. Preferably water is present in a concentration of 5 to 99%, more preferably from 20 to 80%, still more preferably from 40 and 80% by weight of the composition.

Besides water, organic solvents may also serve as carriers within compositions of the present invention.

Emollients may also be used as cosmetically acceptable carriers in the composition of the present invention. Emollients are generally in the form of silicone oils and synthetic esters. Silicone oils may be volatile and non-volatile. Volatile silicone oils are preferably chosen from cyclic or linear polydimethylsiloxanes containing from 3 to 9, preferably from 4 to 5, silicon atoms. Non-volatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes.

Ester emollients that may be used are:
1. Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
2. Ether-esters such as fatty acid esters of ethoxylated fatty alcohols.
3. Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
4. Wax esters such as beeswax, spermaceti, myristyl myristate, stearyl stearate and arachidyl behenate.
5. Sterols esters, of which cholesterol fatty acid esters are examples.

Emollients may be present in the composition anywhere from 0.1 to 50%, preferably from 1 to 20% by weight of the composition.

Fatty acids having from 10 to 30 carbon atoms may also be included as cosmetically acceptable carriers in the composition of this invention. Illustrative examples of such fatty acids are pelargonic, lauric, myristic, palmitic, stearic, isostearic, hydroxystearic, oleic, linoleic, ricinoleic, arachidic, behenic, erucic acids and mixtures thereof.

Humectants of the polyhydric alcohol type may also be employed as cosmetically acceptable carriers in the composition of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The concentration of humectant in the composition may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modfied acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Concentration of the thickener in the composition may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.8%, preferably from 80 to 99% by weight of the composition.

Surfactants may also be present in the composition of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di- fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Sunscreens include those materials commonly employed to block ultraviolet light.

Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation. Additives that reflect or scatter the sun rays may also be employed. These additives include oxides like zinc oxide and titanium dioxide.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include:

antioxidants, binders, biological additives, buffering agents, colorants, polymers, astringents, fragrance, opacifying agents, conditioners, exfoliating agents, pH adjusters, preservatives, natural extracts, essential oils, skin sensates, skin soothing agents, and skin healing agents.

When making the composition of the present invention, the desired ingredients are mixed in no particular order and usually at temperatures from about 70 to about 80° C. and under atmospheric pressure.

The packaging for the composition of this invention can be a patch, bottle, tube, roll-ball applicator, propellant driven aerosol device, squeeze container or lidded jar.

In a second aspect, the invention relates to use of the composition according to the invention for skin lightening.

In a third aspect, the invention relates to a method of lightening the skin of a human, the method comprising the step of applying the composition according to the invention onto the skin.

The invention will now be illustrated by means of the following non-limiting examples.

EXAMPLES

Example 1: In-Vitro Studies on the Effect of the Combination of Niacinamide and Picolinamide on Melanin Inhibition Using Melanin Content Assay (MCA)—an In-House Developed Method Materials
(i) Human primary neonatal foreskin melanocytes (Cat No: HEMn-DP-C-202-5C),
(ii) Melanocyte growth medium (MGM) (Cascade Biologicals, Cat No: M-254-500) and
(iii) Human melanocyte growth supplement (Cat No: S-0002-5) (Cascade Biologicals)
(iv) Picolinamide (Sigma Aldrich, Cat No:104051-10G)
(v) Niacinamide (Sigma, Cat No: N0636-100G)
(vi) DMSO -Dimethyl sulphoxide (Sigma, Cat No D2650)
(vii) NaOH (Merck, Cat No 61757305001730)

Method

Human primary melanocytes were grown in melanocytes growth medium (MGM) with human melanocyte growth supplement. 500 μL/well (5×10$^4$ cells/well) of this solution was plated in a 24 wells plate and incubated in an incubator (Thermo Scientific, Model 3111) at 37° C. with 5% $CO_2$ atmosphere. After 24 hours of incubation, cell cultures were treated with the lead actives dissolved in water. The control was cells treated with the vehicle (water) alone. The cells were again incubated for 72 hours in an incubator (Thermo Scientific, Model 3111; conditions: 5% CO2, at 37° C.). At the end of the incubation the culture medium was replaced with 120μl/well of MCA reagent (10A % DMSO in 1N NaOH) and incubated for 1 hour at 60° C. in a shaker incubator. The supernatant was then transferred to a 384 well plate. The absorbance was measured spectrophotometric at 405 nm with a micro plate reader (GEnios Pro, Tecan).

Calculation of Melanin Content:

The spectrophotometric OD at 405 nm for untreated cells (NO active) was considered as 100% melanin content. In comparison to the untreated cells, the percentage inhibition of the treated cell samples were calculated.

Results

TABLE I

| Set | Sample | % Inhibition in Melanin Synthesis (Mean ± SD) |
|---|---|---|
| 1 | Control | 00 |
| 2 | 5 mM Niacinamide | 3 ± 0.4 |
| 3 | 10 mM Niacinamide | 8 ± 2.3 |
| 4 | 5 mM Picolinamide | 14 ± 0.9 |
| 5 | 10 mM Picolinamide | 23 ± 3.3 |
| 6 | 5 mM Niacinamide + 5 mM Picolinamide | 26 ± 1.4 |
| 7 | 10 mM Niacinamide + 10 mM Picolinamide | 34 ± 0.5 |

The above table (table I) illustrates the synergistic reduction of melanin content in melanocytes obtained by the combination of picolinamide and niacinamide. The data in table I shows that niacinamide by itself gave a modest reduction (at 5 mM and 10 mM) of melanin content in primary human melanocytes. However, when picolinamide and niacinamide were combined, synergistic reduction in melanin content was obtained.

Under in-vivo conditions, skin colour is determined by two processes, melanin synthesis and melanosome transfer. It is thought that regulating these processes will regulate the skin colour. The above example illustrates the synergistic effect the combination of the invention has on the melanin content in the melanocytes in-vitro, and same effect can be expected on melanin synthesis under in-vivo conditions.

Example 2: In-Vitro Studies on the Effect of the Combination of Niacinamide and Picolinamide on Melanosome Transfer Using Melanosome Transfer Assay (MTA) (Pigment Cell Melanoma Res. 2008 October; 21(5):559-64)

Materials
(i) Human primary neonatal foreskin melanocytes (Cat No: HEMn-DP-C-202-5C),
(ii) Melanocyte growth medium (MGM) (Cascade Biologicals, Cat No: M-254-500) and
(iii) Human melanocyte growth supplement (Cascade Biologicals, Cat No: S-0002-5)
(iv) HaCat human keratinocytes (Dr NE Fusenig, Hedelberg, Germany)
(v) Keratinocyte growth medium (KGM) (Cascade Biologicals, Cat No: Epilife MEPI-500CA) and
(vi) Human Keratinocyte growth supplement (Cascade Biologicals, Cat No: F-001-5)
(vii) Picolinamide (Sigma Aldrich, Cat No: 104051-50G)
(viii) Niacinamide (Sigma, Cat No: N0636-100G)
(ix) Trypsin EDTA buffer (Gibco; Catalog No: R-001)
(x) Trypsin neutralizer (Gibco; Catalog No: R-002)
(xi) Para-formladehyde (Sigma Aldrich; 15-812-7)
(xii) Phosphate buffer saline (PBS)
  a. Sodium chloride (Fischer Scientific; Catalog No: 27605)
  b. Potassium chloride (Merck; 61753305001730)
  c. Disodium Hydrogen phosphate (S.D Fine-Chemicals Ltd; Product No: 40158)
  d. Potassium dihydrogen phosphate (S.D Fine Chemicals Ltd, 20203)
(xiii) FACS buffer
  a. Saponin (sigma, catalog: 47036-50G-F)
  b. Fetal Bovine serum (Gibco; Catalog No: 16000)

Method $1.3 \times 10^4$ cells of human primary melanocytes (C-202-5C, Lonza) prepared in culture medium (MGM:KGM=1:1) and $2.6 \times 10^4$ HaCat keratinocytes prepared in culture medium (MGM:KGM=1:1) were mixed together and plated in a 48 well plate and incubated in an tissue culture incubator (Thermo Scientific, Model 3111) at 37° C. with 5% $CO_2$ atmosphere. After 4 hours of incubation, co-cultures were treated (added) with the samples and again incubated for 72 hours in the same incubator under the same conditions. After culturing for required period (72 hours), the cells were prepared for flow cytometry analysis by following the procedure as set out below:

1. Cells were isolated from 48 wells plate into a V-bottom plate (Torson, 941396) with 200 µl of trypsin EDTA buffer and the trypsin activity was neutralized with 200 µl of trypsin neutralizer and pelleted down to 350 g using a cold centrifuge (Plasto Crafts, Model no: Roat 4R-V/FM).
2. To the pellet, 100 µl of 1% para-formaldehyde was added and incubated for 10 minutes on ice.
3. Cells were then centrifuged (1000G with 100 µl of phosphate buffer saline (PBS) for 10 minutes and the pellet was used for staining with a solution as stated in below step 4. The PBS was prepared by adding 4 g sodium chloride, 0.1 g potassium chloride, 0.58 g disodium hydrogen phosphate and 0.1 g potassium dihydrogen phosphate into 500 ml of autoclaved Mili-Q water.

FACS (Florescence activated cell sorter) was prepared by adding 0.1% Saponin and >0.05% (0.05% wt/volume) Fetal Bovine serum in PBS mixed with Alexa 488 conjugated goat anti-Trp1 antibody (TRP1 Alexa 488 (TRP1, tyrosinase related protein is an specific melanosome marker protein, Santacruz, catalog No: sc-10443) (1 µL/100 µL) and anti-pan cytokeratin antibody (pan cytokeratin, cytokeratin is a specific marker for keratinocytes) PE, Santacruz, catalog No: sc-8018) (1 µL/100 µL). The above mention FACS buffer was added to the pellet in each well (100 µL/well) and incubated for 60 minutes on ice.

4. The cells were then washed with PBS and centrifuged down to 1000 g using a cold centrifuge (Plasto crafts, Roat 4R-V/FM)
5. The cell pellets were suspended in PBS and transferred to round bottom 96 wells plate and analysed by flow cytometry (BD Biosciences, Model—BD Facscalibur with BD HTS)

Calculation of Melanosome Transfer (% Transfer):

Keratinocytes containing transferred melanosomes were detected by flow cytometry analysis.

% Inhibition Calculation:

The % transfer in untreated cells (NO active) was considered as 100%. In comparison to the untreated cells, the percentage transfer of the treated cell samples were calculated.

Results

TABLE II

| Set | Sample | % inhibition in keratinocytes containing melanosome (Mean ± SD) |
|---|---|---|
| 8 | Control | 0 ± 0 |
| 9 | Niacinamide 5 mM | 15.1 ± 0.4 |
| 10 | Picolinamide 5 mM | −5 (no inhibition) ± 2 |
| 11 | Picolinamide 5 mM + Niacinamide 5 mM | 26.0 ± 1.7 |

The above table (table II) illustrates the synergistic reduction in keratinocytes containing melanosomes obtained by the combination of picolinamide and niacinamide.

Under in-vivo conditions, skin colour is determined by two processes, melanin synthesis and melanosome transfer from melanocytes to keratinocytes. It is thought that regulating these processes will regulate the skin colour. The above example illustrates the synergistic effect the combination of the invention has on the transfer of melanosomes from melanocytes to keratinocytes in-vitro, and same effect can be expected to influence the melanosome transfer in-vivo.

Example 3: In-Vitro Studies on the Effect of the Combination of Niacinamide and Picolinamide on Melanosome Transfer Using Melanosome Transfer Assay (MTA) (Pigment Cell Melanoma Res. 2008 October; 21 (5):559-64)

Materials (i) Human primary neonatal foreskin melanocytes (Cat No: HEMn-DP-C-202-5C), (ii) Melanocyte growth medium (MGM) (Cascade Biologicals, Cat No: M-254-500) and (iii) Human melanocyte growth supplement (Cascade Biologicals, Cat No: S-0002-5)

(iv) HaCat human keratinocytes (a kind gift from Dr NE Fusenig, Hedelberg, Germany)

(v) Keratinocyte growth medium (KGM) (Cascade Biologicals, Cat No: Epilife MEPI-500CA) and (vi) Human Keratinocyte growth supplement (Cascade Biologicals, Cat No: F-001-5)

(vii) Picolinamide (Sigma Aldrich, Cat No: 104051-50G)

(viii) Niacinamide (Sigma, Cat No: N0636-100G)

(ix) Trypsin EDTA buffer (Gibco; Catalog No: R-001)

(x) Trypsin neutralizer (Gibco; Catalog No: R-002)

(xi) Para-formladehyde (Sigma Aldrich; 15-812-7)

(xii) Phosphate buffer saline (PBS)
  a. Sodium chloride (Fischer Scientific; Catalog No: 27605)
  b. Potassium chloride (Merck; 61753305001730)
  c. Disodium Hydrogen phosphate (S.D Fine-Chemicals Ltd; Product No: 40158)
  d. Potassium dihydrogen phosphate (S.D Fine Chemicals Ltd, 20203)

(xiii) FACS buffer
  a. Saponin (sigma, catalog: 47036-50G-F)
  b. Fetal Bovine serum (Gibco; Catalog No: 16000)

Method $1.3 \times 10^4$ cells of human primary melanocytes (C-202-5C, Lonza) prepared in culture medium (MGM:KGM=1:1) and $2.6 \times 10^4$ HaCat keratinocytes prepared in culture medium (MGM:KGM=1:1) were mixed together and plated in a 48 well plate and incubated in an tissue culture tissue culture incubator (Thermo Scientific, Model 3111) at 37° C. with 5% $CO_2$ atmosphere. After 4 hours of incubation, co-cultures were treated with the samples and again incubated for 72 hours in the same incubator under the same conditions. After culturing for required period (72 hours), the cells were prepared for flow cytometry analysis by following the procedure as set out below:

1. Cells were isolated from 48 wells plate into a V-bottom plate (Torson, 941396) with 200 µl of trypsin EDTA buffer and the trypsin activity was neutralized with 200 µl of trypsin neutralizer and pelleted down to 350 g using a cold centrifuge (Plasto Crafts, Model no: Roat 4R-V/FM).
2. To the pellet, 100 µl of 1% para-formaldehyde was added and incubated for 10 minutes on ice.
3. Cells were then centrifuged (1000 G) with 100 µl of phosphate buffer saline (PBS) for 10 minutes and the pellet was used for staining with a solution as stated in below step 4. The PBS was prepared by adding 4 g sodium chloride, 0.1 g potassium chloride, 0.58 g disodium hydrogen phosphate and 0.1 g potassium dihydrogen phosphate into 500 ml of autoclaved Mili-Q water.

FACS buffer (Florescence activated cell sorter) was prepared by adding 0.1% Saponin and >0.05% (0.05% wt/volume) Fetal Bovine serum in PBS mixed with Alexa 488 conjugated goat anti-Trp1 antibody (TRP1 Alexa 488 (TRP1, tyrosinase related protein is an specific melanosome marker protein, Santacruz, catalog No: sc-10443) (1 µL/100 µL) and anti-pan cytokeratin antibody (pan cytokeratin, cytokeratin is a specific marker for keratinocytes) PE, Santacruz, catalog No: sc-8018) (1 µL/100 µL). The above mention FACS buffer was added to the pellet in each well (100 µL/well) and incubated for 60 minutes on ice.

4. The cells were then washed with PBS and centrifuged down to ~1000 G using a cold centrifuge (Plasto crafts, Roat 4R-V/FM)
5. The cell pellets were suspended in PBS and transferred to round bottom 96 wells plate and analyzed by flow cytometry (BD Biosciences, Model—BD Facs calibur with BD HTS)

Calculation of Melanosome Transfer (% Transfer):

Keratinocytes containing transferred melanosomes were detected by flow cytometry analysis.

% Inhibition Calculation:

The % transfer in untreated cells (NO active) was considered as 100%. In comparison to the untreated cells, the percentage transfer of the treated cell samples were calculated.

Results

TABLE III

| Treatment | Ratio | % Inhibition in melanosome transfer | SD |
|---|---|---|---|
| Picolinamide 5 mM | — | −8 | 3.78 |
| Picolinamide 10 mM | — | 18 | 3.5 |
| Picolinamide 15 mM | — | cell death | 0 |
| Picolinamide 5 mM + Niacinamide 0.315 mM | 16:1 | −1 | 0.89 |
| Picolinamide 5 mM + Niacinamide 0.6255 mM | 8:1 | 7.9 | 0.58 |
| Picolinamide 5 mM + Niacinamide 1.25 mM | 4:1 | 11.3 | 0.54 |
| Picolinamide 6.25 mM + Niacinamide 5 mM | 1.25:1 | 56.9 | 2.3 |
| Picolinamide 5 mM + Niacinamide 5 mM | 1:1 | 29.8 | 4.0 |
| Picolinamide 5 mM + Niacinamide 6.25 mM | 1:1.25 | 31 | 0.02 |
| Picolinamide 1.25 mM + Niacinamide 5 mM | 1:4 | 36.4 | 4.8 |
| Picolinamide 0.6255 mM + Niacinamide 5 mM | 1:8 | 35 | 4.2 |
| Niacinamide 5 mM | — | 16.5 | 2 |
| Niacinamide 10 mM | — | 25 | 3.5 |
| Niacinamide 15 mM | — | cell death | 0 |

The above table (table III) shows the synergistic skin lightening effect is obtained only at specific molar ratios of picolinamide to niacinamide.

The invention claimed is:

1. A skin lightening composition comprising:
   a 0.1 to 10% by weight of picolinamide; and
   b 0.1 to 10% by weight of niacinamide;
   wherein the molar ratio of picolinamide to niacinamide is 1.25 to 1.
2. The skin lightening composition according to claim 1 wherein the composition comprises 1 to 5% by weight of picolinamide.
3. The skin lightening composition according to claim 1, wherein the composition comprises 1 to 5% by weight of niacinamide.
4. The skin lightening composition according to claim 1, further comprising a skin benefit agent.

5. The skin lightening composition according to claim 1 wherein the composition is a topical composition.

6. The composition according to claim 1 wherein the composition further comprises natural extracts.

7. The composition according to claim 1 wherein the picolinamide and niacinamide are present in amounts to achieve a synergistic skin lightening effect.

8. A topical skin lightening composition comprising picolinamide and niacinamide and in amounts to achieve a synergistic skin lightening effect, in a molar ratio of picolinamide to niacinamide of 1.25 to 1.

* * * * *